(12) United States Patent
May et al.

(10) Patent No.: US 6,884,816 B2
(45) Date of Patent: Apr. 26, 2005

(54) HYDROXY SUBSTITUTED FUSED NAPHTHYL-AZOLES AND FUSED INDENO-AZOLES AND THEIR USE FOR THE TREATMENT OF GLAUCOMA

(75) Inventors: Jesse A. May, Fort Worth, TX (US); Paul W. Zinke, Fort Worth, TX (US)

(73) Assignee: Alcon, Inc., Hunenberg (CH)

(*) Notice: Subject to any disclaimer, the term of this patent is extended or adjusted under 35 U.S.C. 154(b) by 59 days.

(21) Appl. No.: 10/231,699

(22) Filed: Aug. 30, 2002

(65) Prior Publication Data

US 2003/0083346 A1 May 1, 2003

Related U.S. Application Data

(60) Provisional application No. 60/316,391, filed on Aug. 31, 2001.

(51) Int. Cl.$^7$ .................... A61K 31/416; C07D 231/54; A61P 27/00
(52) U.S. Cl. .................... 514/405; 548/359.1
(58) Field of Search .................. 548/359.1; 514/405

(56) References Cited

U.S. PATENT DOCUMENTS

| | | | |
|---|---|---|---|
| 4,690,931 A | | 9/1987 | Wick et al. |
| 4,985,424 A | | 1/1991 | Van Wijngaarden et al. |
| 5,296,504 A | | 3/1994 | Stjernschantz et al. |
| 5,352,708 A | | 10/1994 | Woodward et al. |
| 5,422,368 A | | 6/1995 | Stjernschantz et al. |
| 5,494,928 A | | 2/1996 | Bös |
| 5,561,150 A | * | 10/1996 | Wichmann .................. 514/406 |
| 5,571,833 A | | 11/1996 | Kruse et al. |
| 5,578,612 A | | 11/1996 | Macor et al. |
| 5,646,173 A | | 7/1997 | Bös et al. |
| 5,874,477 A | | 2/1999 | McConnell et al. |
| 5,889,052 A | | 3/1999 | Klimko et al. |
| 5,902,815 A | | 5/1999 | Olney et al. |

FOREIGN PATENT DOCUMENTS

| | | | | |
|---|---|---|---|---|
| WO | WO 98/18458 | * | 5/1998 | |
| WO | WO 00/12475 | | 3/2000 | |
| WO | WO 00/16761 | * | 3/2000 | |
| WO | WO 01/85152 A2 | | 11/2001 | .......... A61K/31/00 |

OTHER PUBLICATIONS

"Nonlinear regression using spreadsheets", Wayne P. Bowen, et al., "Principles"–Trends in Pharmacological Sciences, no date, 5 pages.

"Method For the Synthesis of 2–Unsubstituted Tryptamines", I. I. Grandberg et al., Chem. Heterocycl. Compd. (English Transl.) 9,196 (1973).

"Role of 5–$HT_{2A}$ and 5–$HT_{2C}$–receptors in the stimulus effects of hallucinogenic drugs II: reassessment of LSD false positives", David Fiorella, Richard A. Rabin, and J.C. Winter, Psychopharmacology (1995) 121:357–363.

"Pyrrolo[3,2,1–ij]quinoline Derivatives, a 5–$HT_{2c}$ Receptor Agonist with Selectivity over the 5–$HT_{2a}$ Receptor: Potential Therapeutic Applications for Epilepsy and Obesity", Methvin Isaac et al., Bioorganic & Medicinal Chemistry Letters 10 (2000) 919–921.

"Binding to the Serotonin 5–$HT_2$ Receptor by the Enantiomers of 125I–DOI", M. P. Johnson, A. J. Hoffman, D. E. Nichols, and C.A. Mathis, Neuropharmacology vol. 26, No. 12, pp. 1803–1806, (1987).

"Do Beta–Adrenoceptors and Serotonin 5–$HT_{1A}$ Receptors Have Similar Functions in the Control of Intraocular Pressure in the Rabbit?", N. N. Osborne and G. Chidlow, Ophthalmologica (1996), 210:308–314.

"Some 5,6–Dihydro–4H–pyrrolo[3,2,1–ij]quinolines", Edgar A. Steck (1a), and Lynn T. Fletcher (1b), with Clarissa D. Carabateas, Sterling–Winthrop Research Institute, Rensselaer, New York 12144, (Jun. 1974), pp. 387–393.

"Effect of 5–methylurapidil, an $\alpha_{1a}$–adrenergic antagonist and 5–hydroxytryptamine$_{1a}$ agonist, on aqueous humor dynamics in monkeys and rabbits", Rong–Fang Wang, Ping–Yu Lee, Thomas W. Mittag, Steven M. Podos and Janet B. Serle, Department of Ophthalmology, Mount Sinai School of Medicine, New York, USA, Current Eye Research 16, 769 (1997), pp. 769–775.

"Effect of p–MPPI Hydrochloride (p–MPPI) Applied Before 5–Methylurapidil (5–MU) on Intraocular Pressure (IOP) in Normal Monkeys", R–F Wang, Thom Mittag, S. M. Podos, J.B. Serle, Abstract 2236–B93, Department of Opthalmology, Mount Sinai School of Medicine, Mount Sinai School of Medicine, New York, NY., p. S488.

* cited by examiner

*Primary Examiner*—Rita Desai
*Assistant Examiner*—Robert Shiao
(74) *Attorney, Agent, or Firm*—Kilyk & Bowersox, P.L.L.C.

(57) ABSTRACT

Hydroxy substituted fused naphthyl-azoles and fused indeno-azoles are disclosed. Also disclosed are methods for the lowering and controlling of normal or elevated intraocular pressure as well as a method for the treatment of glaucoma using compositions containing one or more of the compounds of the present invention.

22 Claims, No Drawings

HYDROXY SUBSTITUTED FUSED NAPHTHYL-AZOLES AND FUSED INDENO-AZOLES AND THEIR USE FOR THE TREATMENT OF GLAUCOMA

This application claims the benefit of U.S. Provisional Patent Application No. 60/316,391 filed Aug. 31, 2001, and is incorporated in its entirety by reference herein.

BACKGROUND OF THE INVENTION

The present invention relates to various indazoles and indoles. Preferably the present invention is directed to the use of substituted 2-(benzo[g]indazol-1-yl)-ethylamines and 1-(4H-indeno[1,2-c]pyrazol-1-yl)-1-methylethylamines. These compounds are useful for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but due to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds are 5-$HT_{1B,D,E,F}$ agonists, e.g., sumatriptan and naratriptan and related compounds.

It has been found that serotonergic compounds which possess agonist activity at 5-$HT_2$ receptors effectively lower and control normal and elevated IOP and are useful for treating glaucoma, see commonly owned co-pending application, PCT/US99/19888, incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121:357,1995].

U.S. Pat. No. 5,561,150 relates to substituted 2-(benzo[g] indazol-1-yl)-1-ethylamines and 2-(4H-indeno[1,2-c] pyrazol-1-yl)-1-ethylamine having preferential affinity for the 5-$HT_{2C}$ receptor as well as affinity for the 5-$HT_{2A}$ receptor. Further, it is mentioned that these compounds have utility for certain central nervous system disorders of therapeutic significance.

U.S. Pat. No. 5,646,173 relates to certain tricyclic pyrazole derivative compounds which are identified as being 5-$HT_{2C}$ agonists for the treatment of CNS diseases and are primarily directed to lipophilic analogs that have a high probability of entering the brain. Similarly, WO 98/56768 relates to tricyclic 5-$HT_{2C}$ agonists for the treatment of CNS diseases.

All of the patents, patent applications, and publications mentioned above and throughout are incorporated in their entirety by reference herein and form a part of the present application.

5-Hydroxytryptamine (serotonin) does not cross the blood-brain barrier and enter the brain. However, in order to increase brain serotonin levels the administration of 5-hydroxy-tryptophane can be employed. The transport of 5-hydroxy-tryptophane into the brain readily occurs, and once in the brain 5-hydroxy-tryptophane is rapidly decarboxylated to provide serotonin. Since the treatment of glaucoma is preferably with compounds that do not enter the CNS, relatively polar compounds that are 5-$HT_2$ agonists and have incorporated into their structure a phenolic hydroxyl group that can be considered comparable to that of serotonin, are of particular interest.

The chemical synthesis of 2-(4H-pyrrolo[3,2,1-ij] quinolin-1-yl)-ethylamine has been reported [J. Heterocyclic Chem. 11, 387 (1974), Chem. Heterocycl. Compd. (Engl. Transl.) 9, 196 (1973)] with no mention of utility. The synthesis of selected 2-(4H-pyrrolo[3,2,1-ij]quinolin-1-yl)-ethylamine derivatives, such as 2-(8-fluoro-5,6-dihydro-4H-pyrrolo[3,2,1-ij]quinolin-1-yl)-ethylamine, has been reported [Bioorg. Med. Chem. Lett. 10, 919 (2000)]. It was suggested that such compounds could have utility in the treatment of epilepsy and obesity. The preparation of 1- and 2-substituted 2H-indeno[1,2,3-cd]indazoles is disclosed in Belg. 718,057 (1968); these compounds are noted as having psychotherapeutic activity. Various ring substituted amides and esters of 7,8-dihydro-6H-pyrazolo[4,5,1-ij]quinoline-2-carboxylic acid have been disclosed as antagonists at 5-HT$_3$ receptors [U.S. Pat. No. 4,985,424].

Accordingly, there is a need to provide compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are preferably 5-HT$_2$ agonists.

A feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to methods to lower and/or control normal or elevated intraocular pressure by administering an effective amount of a composition containing a compound having Formula I as described below:

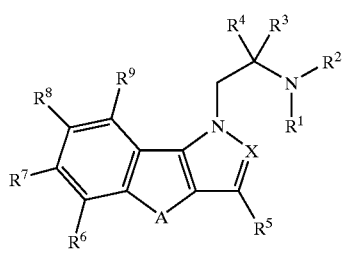

Formula I wherein R$^1$ and R$^2$ are independently hydrogen;

R$^3$ and R$^4$ are independently chosen from hydrogen, an alkyl group such as C$_{1-4}$alkyl, or R$^3$, R$^4$ and the carbon atom to which they are attached can form a cyclopropyl ring, or furthermore, R$^2$ and R$^3$ together can be (CH$_2$)$_m$ to form a saturated heterocycle; and when R$^2$ and R$^3$ are part of a heterocycle, R$^1$ can be hydrogen or an alkyl group such as a C$_{1-4}$alkyl;

R$^5$ is chosen from hydrogen, halogen, or an unsubstituted or substituted alkyl group, such as C$_{1-4}$alkyl or C$_{1-4}$alkyl substituted with halogen;

R$^6$–R$^9$ are independently chosen from hydrogen, halogen, an unsubstituted or substituted alkyl group, an unsubstituted or substituted alkoxy group, or hydroxyl group, such as C$_{1-4}$alkyl, C$_{1-4}$alkoxy, hydroxyl, or C$_{1-4}$alkyl substituted by halogen;

A is CH$_2$CH$_2$, CH=CH, or CR$^{10}$R$^{11}$;

X is either N or CH;

R$^{10}$ and R$^{11}$ are hydrogen, an unsubstituted or substituted alkyl group, such as C$_{1-4}$alkyl, or halogen;

m is 3 or 4;

and pharmaceutically acceptable salts and solvates of the compounds of Formula I.

In preferred aspects of the invention, at least one of R$^3$ or R$^4$ is an alkyl group such as C$_{1-4}$alkyl. Preferably, at least one of R$^3$ or R$^4$ is a methyl group. Most preferably, R$^3$ is a methyl group.

The present invention also relates to a method for treating glaucoma which involves administering an effective amount of a composition containing a compound having Formula I as described above.

The present invention further relates to the use of pharmaceutical compositions containing at least one compound of Formula I.

In addition, the present invention relates to compounds represented by Formula I:

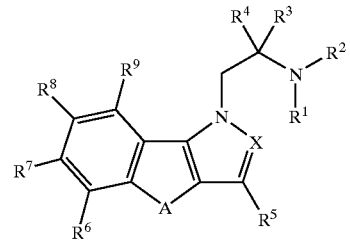

a) wherein R$^1$ is a hydrogen or a substituted or unsubstituted alkyl group;

R$^2$ and R$^3$ together represent (CH$_2$)$_m$ to form a saturated heterocycle;

R$^5$ is chosen from hydrogen, halogen, or a substituted or unsubstituted alkyl group;

R$^6$–R$^9$ are independently chosen from hydrogen, halogen, a substituted or unsubstituted alkyl group, a substituted or unsubstituted alkoxy group, or hydroxyl;

A is CH$_2$CH$_2$, CH=CH, or CR$^{10}$R$^{11}$;

X is N or CH;

R$^{10}$ and R$^{11}$ are independently hydrogen, a substituted or unsubstituted alkyl group, or halogen;

m is 3 or 4;

or pharmaceutically acceptable salts or solvates thereof; or b) wherein R$^1$ and R$^2$ are hydrogen;

R$^3$, R$^4$ and the carbon atom to which they are attached form a cyclopropyl ring;

R$^5$ is chosen from hydrogen, halogen, or a substituted or unsubstituted alkyl group;

R$^6$–R$^9$ are independently chosen from hydrogen, halogen, a substituted or unsubstituted alkyl group, a substituted or unsubstituted alkoxy group, or hydroxyl;

A is CH$_2$CH$_2$, CH=CH, or CR$^{10}$R$^{11}$;

X is N or CH;

$R^{10}$ and $R^{11}$ are independently hydrogen, a substituted or unsubstituted alkyl group, or halogen;

m is 3 or 4;

or pharmaceutically acceptable salts or solvates thereof; or c) wherein $R^1$ and $R^2$ are hydrogen; or $R^1$ is a hydrogen or a substituted or unsubstituted alkyl group when $R^2$ and $R^3$ are part of a heterocycle;

$R^3$ and $R^4$ are independently chosen from hydrogen, or $R^3$, $R^4$ and the carbon atom to which they are attached form a cyclopropyl ring, or $R^2$ and $R^3$ together represent $(CH_2)_m$ to form a saturated heterocycle;

$R^5$ is chosen from hydrogen, halogen, or a substituted or unsubstituted alkyl group;

$R^6$–$R^9$ are independently chosen from hydrogen, halogen, a substituted or unsubstituted alkyl group, a substituted or unsubstituted alkoxy group, or hydroxyl;

A is $CH_2CH_2$, CH=CH, or $CR^{10}R^{11}$;

X is N or CH;

$R^{10}$ and $R^{11}$ are independently hydrogen, a substituted or unsubstituted alkyl group, or halogen;

m is 3 or 4; wherein at least one of $R^5$, $R^{10}$, or $R^{11}$ is a halogen or pharmaceutically acceptable salts or solvates thereof; or d) wherein $R^1$ and $R^2$ are hydrogen; or $R^1$ is a hydrogen or a substituted or unsubstituted alkyl group when $R^2$ and $R^3$ are part of a heterocycle;

$R^3$ and $R^4$ are independently chosen from hydrogen, or $R^3$, $R^4$ and the carbon atom to which they are attached form a cyclopropyl ring, or $R^2$ and R together represent $(CH_2)_m$ to form a saturated heterocycle;

$R^5$ is chosen from hydrogen, halogen, or a substituted or unsubstituted alkyl group;

$R^6$–$R^9$ are independently chosen from hydrogen, halogen, a substituted or unsubstituted alkyl group, a substituted or unsubstituted alkoxy group, or hydroxyl;

A is $CH_2CH_2$, CH=CH, or $CR^{10}R^{11}$;

X is CH;

$R^{10}$ and $R^{11}$ are independently hydrogen, a substituted or unsubstituted alkyl group, or halogen;

m is 3 or 4;

or pharmaceutically acceptable salts or solvates thereof.

It is to be understood that both the foregoing general description and the following detailed description are exemplary and explanatory only and are intended to provide a further explanation of the present invention, as claimed.

DETAILED DESCRIPTION OF THE INVENTION

The present invention relates to a variety of compounds that are useful according to the present invention. These compounds are generally represented by the following Formula I:

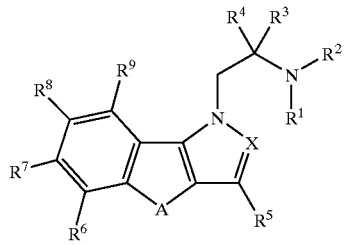

Formula I wherein $R^1$ and $R^2$ are independently hydrogen;

$R^3$ and $R^4$ are independently chosen from hydrogen, an alkyl group such as $C_{1-4}$alkyl, or $R^3$, $R^4$ and the carbon atom to which they are attached can form a cyclopropyl ring, or furthermore, $R^2$ and $R^3$ together can be $(CH_2)_m$ to form a saturated heterocycle; and when $R^2$ and $R^3$ are part of a heterocycle, $R^1$ can be hydrogen or an unsubstituted or substituted alkyl group, such as a $C_{1-4}$alkyl;

$R^5$ is chosen from hydrogen, halogen, or an unsubstituted or substituted alkyl group, such as $C_{1-4}$alkyl or $C_{1-4}$alkyl substituted with halogen;

$R^6$–$R^9$ are independently chosen from hydrogen, halogen, an unsubstituted or substituted alkyl group, an unsubstituted or substituted alkoxy group, or hydroxyl group, such as $C_{1-4}$alkyl, $C_{1-4}$alkoxy, hydroxyl, or $C_{1-4}$alkyl substituted with halogen;

A is $CH_2CH_2$, CH=CH, or $CR^{10}R^{11}$;

X is either N or CH;

$R^{10}$ and $R^{11}$ are independently chosen from hydrogen, halogen, or an unsubstituted or substituted alkyl group, such as $C_{1-4}$alkyl;

m is 3 or 4;

and pharmaceutically acceptable salts and solvates of the compounds of Formula I.

Preferred Compounds are:

Wherein $R^1$ and $R^2$ are hydrogen;
R is $C_{1-4}$alkyl or $R^2$ and $R^3$ together can be $(CH_2)_3$ to form pyrrolidine;
$R^4$ is hydrogen;
$R^5$ is chosen from hydrogen, halogen, $C_{1-4}$alkyl, or $C_{1-4}$alkyl substituted with halogen;
$R^6$–$R^9$ are independently chosen from hydrogen, halogen, $C_{1-4}$alkyl, $C_{1-4}$alkoxy, hydroxyl, or $C_{1-4}$alkyl substituted with halogen;
A is CH=CH, $CH_2CH_2$, or $CR^{10}R^{11}$; and
X is N; or pharmaceutically acceptable salts and solvates of the above preferred compounds.

Most Preferred Compounds are:

Wherein $R^1$ and $R^2$ are hydrogen;
$R^3$ is $C_{1-4}$alkyl;
$R^4$ is hydrogen;
$R^5$ and $R^6$ are independently chosen from hydrogen, halogen, or $C_{1-4}$alkyl;
$R^7$, $R^8$ and $R^9$ are independently chosen from hydrogen, halogen, or hydroxyl;
A is CH=CH or $CH_2CH_2$; and
X is N; or pharmaceutically acceptable salts and solvates of the above preferred compounds.

Representative Examples of Preferred Compounds of Formula I are:

1-(2-Aminopropyl)-4,5-dihydro-1H-benzo[g]indazol-8-ol;
1-(2-Aminopropyl)-1H-benzo[g]indazol-8-ol;
1-(2-Aminopropyl)-1H-benzo[g]indazol-7-ol;
2-(8-Methoxy-benzo[g]indazol-1-yl)-1-methylethylamine;
1-(2-Aminopropyl)-1,4-dihydro-indeno[1,2-c]pyrazol-6-ol; or
1-(2-Aminopropyl)-4,4-dimethyl-1,4-dihydro-indeno[1,2-c]pyrazol-7-ol; or combinations thereof.

It is recognized that compounds of Formula I can contain one or more chiral centers. This invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

In the formulas described above, the alkyl group can be straight-chain, branched, or cyclic and the like. Halogen includes Cl, Br, F, or I. Alkoxy is understood as an alkyl group bonded through an oxygen atom.

Synthesis

The substituted 1-(benzo[g]indazol-2-yl)-1-ethylamine compounds of Formula I can be prepared by using the procedures described in U.S. Pat. No. 5,561,150 (incorporated in its entirety by reference herein) or by the modifications of these procedures as described in Scheme 1. Hydroxymethyleneketone 2 was prepared by addition of ethyl formate to the enolate of tetralone 1. Condensation of enal 2 with the desired substituted ethylaminohydrazine furnished a mixture of two isomeric N-substituted indazoles, which are separated by column chromatography. Protection of the amino group, oxidation with DDQ, and subsequent deprotection affords amine 6.

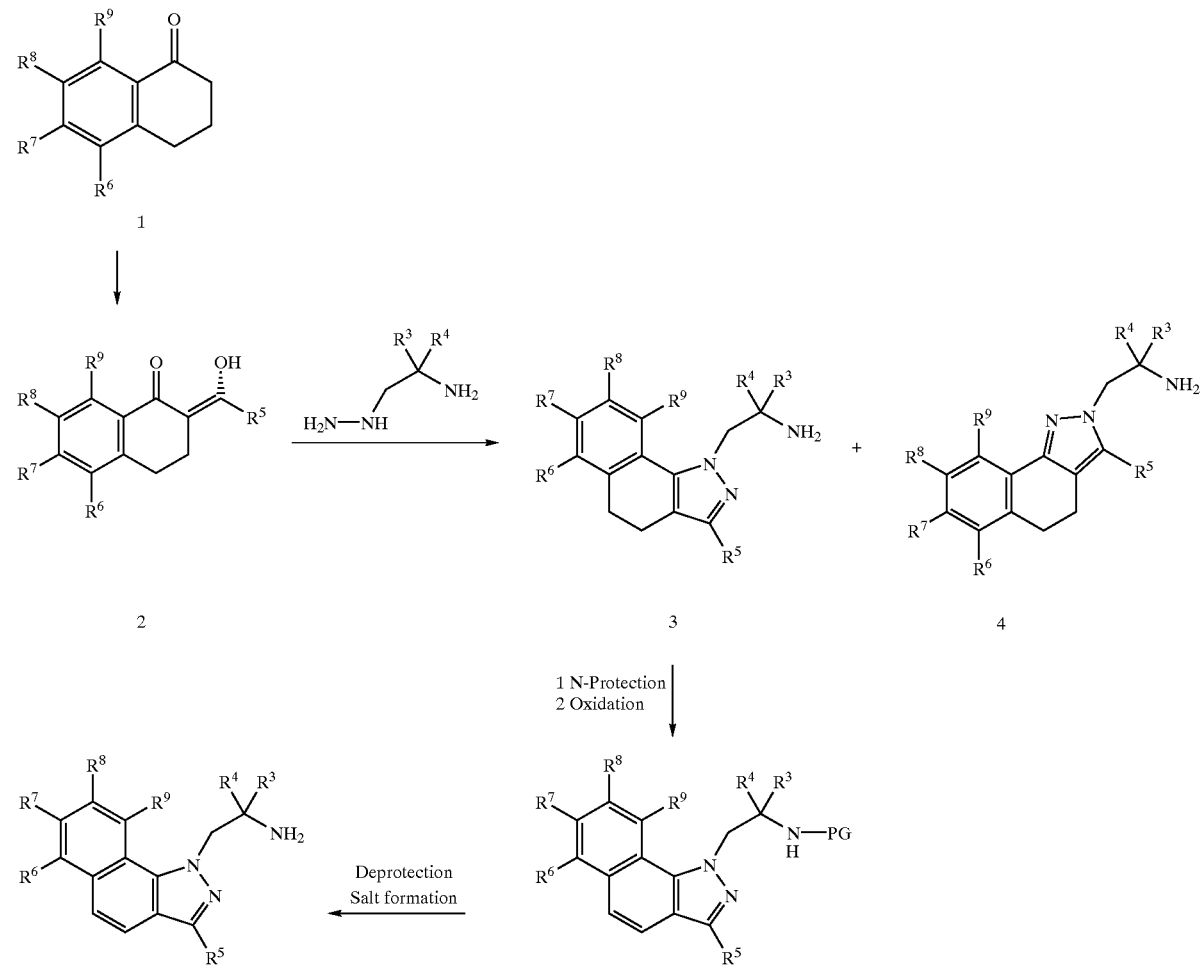

Scheme 1

The preferred compounds of Formula I are described in Examples 2 and 4. The most preferred compound is in Example 4. Examples of formulations anticipated to be suitable for delivery of this compound to the eye are provided.

The compounds of this invention, Formula I, can be incorporated into various types of ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for eating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α1 antagonists (e.g., nipradolol), α2 agonists (e.g. iopidine and brimonidine ), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368 and 5,151,444), "hypotensive lipids" (e.g., lumigan and compounds set forth in U.S. Pat. No. 5,352,708), and neuroprotectants (e.g., compounds from U.S. Pat. No. 4,690,931), particulary eliprodil and R-eliprodil, as set forth in a pending application U.S. S. No. 60/203,350, and appropriate compounds from WO 94/13275, including memantine. All of the patents, applications, and publications are incorporated in their entirety by reference herein.

The compounds of the present invention preferably function as 5-$HT_2$ agonists and preferably do not enter the CNS. In more detail, the particular compounds of the present invention have incorporated into their structure a phenolic hydroxyl group which is considered comparable to that of serotonin and thus the compounds of the present invention preferably do not cross the blood-brain barrier and enter the brain. Compounds having the ability to be a 5-$HT_2$ agonist are beneficial for controlling IOP as well as the treatment of glaucoma as shown in International Published Patent Application No. WO 00/16761, incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma.

The following Examples are given to illustrate the preparation of compounds that are the subject of this invention but should not be construed as implying any limitations to the claims. The proton magnetic resonance spectrum of each compound of the Examples was consistent with the assigned structure.

Method 1

5-$HT_2$ Receptor Binding Assay

To determine the affinities of serotonergic compounds at the 5-$HT_2$ receptors, their ability to compete for the binding of the agonist radioligand [$^{125}$I]DOI to brain 5-$HT_2$ receptors is determined as described below with minor modification of the literature procedure [Neuropharmacology, 26, 1803 (1987)]. Aliquots of post mortem rat or human cerebral cortex homogenates (400 µL) dispersed in 50 mM Tris-HCl buffer (pH 7.4) are incubated with [$^{125}$I]DOI (80 pM final) in the absence or presence of methiothepin (10 µM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the $IC_{50}$ or $K_1$ value.

Method 2

5-$HT_2$ functional Assay: $[Ca^{2+}]_i$ Mobilization

The receptor-mediated mobilization on intracellular calcium ($[Ca^{2+}]_i$) was studied using the Fluorescence Imaging Plate Reader (FLIPR) instrument. Rat vascular smooth muscle cells, A7r5, were grown in a normal media of DMEM/10% FBS and 10 µg/mL gentamycin. Confluent cell monolayers were trypsinized, pelleted, and re-suspended in normal media. Cells were seeded in a 50 µL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 μL) to each well of the 96-well plate and incubated with dye for 1 h at 23° C.

Typically, test compounds were stored at 25 μM in 50% DMSO/50% Ethanol solvent. Compounds were diluted 1:50 in 20% DMSO/20% ethanol. For "hit" screening, compounds were further diluted 1:10 in FLIPR buffer and tested at a final concentration of 10 μM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000–12000 counts by modifying the exposure time, the camera F-stop, or the laser power. Instrument settings for a typical assay were the following: laser power 0.3–0.6 W, camera F-stop F/2, and exposure time 0.4 sec. An aliquot (25 μL) of the test compound was added to the existing 100 μL dye-loaded cells at a dispensing speed of 50 μL/sec. Fluorescence data were collected in real-time at 1.0 sec intervals for the first 60 sees and at 6.0 sec intervals for an additional 120 sees. Responses were measured as peak fluorescence intensity minus basal and where appropriate were expressed as a percentage of a maximum 5-HT-induced response. When the compounds were tested as antagonists against 10 μM 5-HT, they were incubated with the cells for 15 minutes prior to the addition of 5-HT.

The above procedures were used to generate the data shown in Table 1.

TABLE 1

5-HT$_2$ Receptor Binding and Functional Data

| Compound | IC$_{50}$, nM | EC$_{50}$, nM | Efficacy (E$_{max}$, %) |
|---|---|---|---|
| Example 2 | 1.15 | 103 | 46 |
| Example 3 | 1.50 | 285 | 61 |
| Example 4 | 2.10 | 211 | 79 |
| Example 5 | 5.0 | 328 | 64 |
| DOI | 0.33 | 30.2 | 31 |
| 5-HT | 0.941 | 80 | 107 |

EXAMPLE 1

1-(8-Methoxy-4,5-dihydro-benzo[g]indazol-2-yl)-1-methylethylamine dihydrochloride Step A: 1-(8-Methoxy-4,5-dihydro-benzo[g]indazol-1-yl)-1-methylethylamine To a solution of 2-hydroxymethylene-7-methoxy-3,4-dihydro-2H-naphthalen-1-one (0.37 g, 1.8 mmol) in ethanol (15 mL) was added 2-hydrazino-1-methylethylamine (0.16 g, 1.8 mmol) and 1 N HCl (2 mL of a 1:1 mixture of methanol and ethanol). This solution was heated at reflux temperature for 6 h, cooled to 23° C., and stirred for an additional 16 h. The reaction mixture was evaporated to a crude product which was purified by chromatography (silica, gradient, 5% to 10% methanol in dichloromethane) to give an oil (0.19 g, 40%): R$_f$=0.43 (silica, 10% methanol in dichloromethane); $^1$H NMR (CDCl$_3$) δ 7.37 (d, J=2.6 Hz, 1H), 7.20 (s, 1H), 7.12 (d, J 8.2 Hz, 1H), 6.75 (dd, J=8.2, 2.6 Hz, 1H), 4.12 (dd, J=13.6, 4.2 Hz, 1H), 3.9 (m, 1H), 3.88 (s, 3H), 3.5 (bs, 2H), 2.88 (t, J=6.2 Hz, 2H), 2.71 (t, J=6.2 Hz, 2H), 1.14 (d, J=6.4 Hz, 3H). The 2-substituted regioisomer also formed during the cyclization reaction was also isolated (0.11 g, 24%).

Step B: 1-(8-Methoxy-4,5-dihydro-benzo[g]indazol-1-yl)-1-methylethylamine hydrochloride The product from Step A (0.030 g, 0.12 mmol) was dissolved in 0.1 N HCl and the solution was concentrated to give a white solid (0.021 g, 53%): $^1$H NMR (CDCl$_3$) δ 7.50 (s, 1H), 7.35 (d, J=8.4 Hz, 1H), 7.07 (d, J=2.4 Hz, 1H), 6.94 (dd, J=8.4, 2.4 Hz, 1H), 4.7 (m, 2H), 3.86 (m, 1H), 3.83 (s, 3H), 2.78 (t, J=7.2 Hz, 2H), 2.57 (m, 2H) 1.24 (d, J=6.6 Hz, 3H); MS m/z 258 [M+H]$^+$, 241, 201. Analysis. Calculated for C$_{15}$H$_{19}$N$_3$O.2HCl.0.25 H$_2$O: C, 53.82; H, 6.47; N, 12.55. Found: C, 53.86; H, 6.73; N, 12.51.

EXAMPLE 2

1-(2-Aminopropyl)-4,5-dihydro-1H-benzo[g]indazol-8-ol dihydrochloride

To a solution of the product of Step A of Example 1 (0.020 g, 0.78 mmol) in 1,2-dichloroethane (10 mL) was added boron tribromide-dimethylsulfide (1.0 mL, 1.0 mmol), and the solution heated at reflux temperature for 24 hr. The solution was allowed to cool to ambient temperature and the reaction was quenched by the addition of aqueous NaHCO$_3$; this mixture was extracted with chloroform (2×25 mL). The combined extracts were dried (NaSO$_4$), filtered, and evaporated to a crude product which was purified by chromatography (silica, gradient, 10% to 20% methanol in dichloromethane) to provide an oil (0.032 g, 15%). Treatment of the free base with 0.5 N HCl followed by concentration afforded the hydrochloride salt (0.010 g, 24%): $^1$H NMR (D$_2$O) δ 7.56 (s, 1H), 7.34 (d, J=7.8 Hz, 1H), 7.11 (d, J=2.4 Hz, 1H), 6.88 (dd, J=7.8, 2.4 Hz, 1H), 4.70 (m, 1H), 3.9 (m, 1H), 2.83 (m, 2H), 2.67 (m, 2H), 1.31 (d, J=7.2 Hz, 3H); MS m/z: 244 [M+H]$^+$, 187. Analysis. Calculated for C$_{14}$H$_{17}$N$_3$O.2 HCl.1.4 H$_2$O: C, 49.24; H, 6.44; N, 12.31. Found: C, 49.19; H, 6.24; N, 12.41.

EXAMPLE 3

1-(8-Methoxy-benzo[g]indazol-2-yl)-1-methylethylamine dihydrochloride

Step A: [1-(8-Methoxy-4,5-dihydro-benzo[g]indazol-1-yl)-1-methylethyl]-carbamic acid 9H-fluoren-9-ylmethyl ester The crude product from Step A of Example 1 (0.2 g, 0.8 mmol) was dissolved in a 4:1 mixture of 1,4-dioxane and water (5 mL), and NaHCO$_3$ (0.42 g, 5.0 mmol) was added followed by 9-fluorenyl-methylchloroformate (0.26 g, 1.0 mmol), and the mixture stirred at 23° C. for 16 hr. The mixture was poured into dilute aqueous NaHCO$_3$ and extracted with ether (2×20 mL). The combined extracts were dried (MgSO$_4$), filtered and concentrated to a residue which was purified by chromatography (silica, gradient, 20% to 50% ethyl acetate in hexanes) to give an oil (0.10 g, 26%): $^1$H NMR MR (CDCl$_3$) δ 7.75 (d, J=6 Hz, 2H), 7.56 (d, J=6 Hz, 2H), 7.4–7.1 (m, 7H), 6.76 (dd, J=8, 2 Hz, 1H), 5.6 (bs, 1H), 4.53 (m, 1H), 4.2–4.0 (m, 5H), 3.83 (s, 3H), 2.79 (t, J=8 Hz, 2H), 2.67 (t, J=8 Hz, 2H), 1.2 (m, 3H); MS m/z: 480 [M+H]$^+$, 284, 258, 201, 179.

Step B: [1-(8-Methoxy-benzo[g]indazol-1-yl)-1-methylethyl]-carbamic acid 9H-fluoren-9-ylmethyl ester To a solution of the product from Step A (0.08 g, 0.17 mmol) in 1,4-dioxane (10 mL) was added DDQ (0.08 g, 0.34 mmol). The solution was stirred at 23° C. for 3 hr and poured into saturated aqueous NaHCO$_3$ and this mixture was extracted with ether (2×20 mL). The combined extracts were washed with aqueous NaHCO$_3$, dried (MgSO$_4$), and evaporated to a crude product which was purified by chromatography (silica, 40% ethyl acetate in hexanes) to obtain an oil (0.045 g, 55%): MS m/z: 478 [M+H]$^+$.

Step C: 1-(8-Methoxy-benzo[g]indazol-1-yl)-1-methyethylamine dihydrochloride

A solution of the product from Step B (0.045 g, 0.094 mmol) in a mixture of piperidine in DMF (1:4, 5 mL) was stirred for 5 min at 23° C., poured into a saturated aqueous solution of NaHCO$_3$ and extracted with ethyl acetate (2×20 mL). The combined extracts were dried (NaSO$_4$), filtered, and concentrated to a crude product which was purified by chromatography (silica, gradient, 4% to 10% methanol in dichloromethane) to furnish an oil (0.008 g, 71%). The free base was dissolved in 0.1 N aqueous HCl (1 mL) and the solution concentrated to give the dihydrochloride as a white solid (0.0043 g, 34%): $^1$H NMR (CD$_3$OD) δ 8.17 (s, 1H), 8.00 (d, J=9.0 Hz, 1H), 7.90 (d, J=2.2 Hz, 1H), 7.64 (d, J=8.6 Hz, 1H), 7.56 (d, J=8.6 Hz, 2H), 7.4 (d, J=9 Hz, 1H), 5.23 (dd, J=15.2, 4.6 Hz, 1H), 5.06 (dd, J=15.2, 8.2 Hz, 1H), 4.1 (m, 1H), 4.08 (s, 3H), 1.49 (d, J=6.6 Hz, 3H); MS m/z: 256 [M+H]$^+$, 199.

EXAMPLE 4

1-(2-Aminopropyl)-2H-benzo[g]indazol-7-ol

Step A: 2-(7-Methoxy-4,5-dihydrobenzo[g]indazol-1-yl)-1-methylethylamine.

To a solution of 2-hydroxymethylene-6-methoxy-1-tetralone (3.3 g, 16 mmol) in ethanol (10 mL) was added a 1 N solution of HCl in methanol (20 mL) followed by 2-aminopropyl-1-hydrazine (1.78 g, 20 mmol). This mixture was treated in the manner described in Step A of Example 1 to furnish a pale yellow oil (0.60 g, 15%): $^1$H NMR (CDCl$_3$) δ 7.51 (d, J=8.4 Hz, 1H), 7.35 (s, 1H), 6.87 (d, J=1.8 Hz, 1H), 6.82 (dd, J=8.4 Hz, 1.8 Hz, 1H), 4.34 (dd, J=13.8, 4.8 Hz, 1H), 4.20 (dd, J=13.8, 8.4 Hz, 1H), 3.83 (s, 3H), 3.55 (m, 1H), 2.86 (t, J=7.8 Hz, 2H), 2.67 (dd, J=7.8, 6.0 Hz, 2H), 1.17 (d, J=6.6 Hz, 3H); MS m/z 258 [M+H]$^+$.

Step B: [1-(7-Methoxy-4,5-dihydro-benzo[g]indazol-1-yl)-1-methylethyl]-carbamic acid 9H-fluoren-9-ylmethyl ester.

To a solution of the product of Step A (0.34 g, 1.3 mmol) in a mixture of 1,4-dioxane (20 mL) and water (2 mL) containing NaHCO$_3$ (0.84 g, 10 mmol) was added FMOCCl (0.52 g, 2.0 mmol) followed by stirring at 23° C. for 16 h. The reaction mixture was poured into aqueous NaHCO$_3$ and extracted with ethyl acetate (2×20 mL). The combined extracts were dried (MgSO$_4$), and concentrated to a residue, which was purified by chromatography (silica, 40% ethyl acetate in hexanes) to give an oil (0.11 g, 18%): $^1$H NMR (CDCl$_3$) δ 7.8 (m, 3H), 7.6 (m, 3H), 7.4 (m, 2H), 7.2 (m, 3H), 6.8 (m, 2H), 4.4–4.1 (bm, 10H), 3.8 (d, 3H), 2.9–2.6 (m, 4H), 1.3 (m, 3H); MS m/z 480 [M+H]$^+$.

Step C: [1-(7-Methoxy-benzo[g]indazol-1-yl)-1-methylethyl]-carbamic acid 9H-fluoren-9-ylmethyl ester.

To a solution of the product from Step B (0.11 g, 0.23 mmol) in 1,4-dioxane (10 mL) was added DDQ (0.19 g, 0.8 mmol) and the solution stirred at 23° C. for 72 h. The solution was poured into aqueous NaHCO$_3$ and the mixture was extracted with ethyl acetate (2×20 mL). The combined organic extracts were dried (MgSO$_4$) and concentrated to a residue, which was purified by chromatography (silica, 25% ethyl acetate in hexanes) to give an oil (0.1 g, 91%): $^1$H NMR (CDCl$_3$) δ 8.5 (bs, 1H), 8.01 (s, 1H), 7.75 (d, J=6 Hz, 2H), 7.63 (d, J=12 Hz, 1H), 7.5 (bs, 1H), 7.4 (m, 3H), 7.3–7.2 (m, 5H), 5.2 (m, 1H), 5.0 (m, 1H), 4.75 (m, 1H), 4.4–4.3 (m, 2H), 4.1 (m, 1H), 3.93 (s, 3H), 1.21 (t, J=6 Hz, 3H); MS m/z 478 [M+H]$^+$.

Step D: 2-(7-Methoxy-benzo[g]indazol-1-yl)-1-methylethylamine.

A solution of piperidine in DMF (1:4, 5 mL) was added to the product of Step C (0.1 g, 0.2 mmol) and the solution was stirred for 5 minutes at 23° C., poured into aqueous NaHCO$_3$, and extracted with ethyl acetate (2×20 mL). The combined extracts were dried (MgSO$_4$) and concentrated to a residue, which was purified by chromatography (silica, gradient, 3 to 10% methanol in dichloromethane) to give an oil (0.035 g, 64%): $^1$H NMR (CDCl$_3$) δ 8.27 (d, J=9.0 Hz, 1H), 8.01 (s, 1H), 7.64 (d, J=9.0 Hz, 1H), 7.41 (d, J=8.4 Hz, 1H), 7.34 (d, J=2.4 Hz, 1H), 7.26 (m, 1H), 4.76 (dd, J=14.4, 4.8 Hz, 1H), 4.63 (dd, J=14.4, 8.4 Hz, 1H), 3.96 (s, 3H), 3.67 (m, 1H), 1.25 (d, J=6.0 Hz, 3H); MS m/z 256 [M+H]$^+$.

Step E: 1-(2-Aminopropyl)-1H-benzo[g]indazol-7-ol

To a solution of the product from Step D (26 mg, 0.1 mmol) in 1,2-dichloroethane (10 mL) was added boron tribromide-methylsulfide complex (1.0 M, 1.0 mL, 1.0 mmol) and the solution stirred at reflux for 72 h. The solution was poured into aqueous NaHCO$_3$, and extracted with ethyl acetate (2×20 mL). The combined extracts were dried (MgSO$_4$) concentrated to a residue, which was purified by chromatography (silica, gradient, 10 to 25% methanol in dichloromethane) to furnish a solid (8 mg, 32%): $^1$H NMR (CDCl$_3$) δ 8.30 (d, J=9.0 Hz, 1H), 7.99 (s, 1H), 7.60 (d, J=8.4 Hz, 1H), 7.35 (d, J=9.0 Hz, 1H), 7.29 (d, J=2.4 Hz, 1H), 7.21 (dd, J=9.0, 2.4 Hz, 1H), 3.6 (m, 1H), 3.3 (m, 2H), 1.25 (d, J=6.6 Hz, 3H); MS m/z 242 [M+H]$^+$.

EXAMPLE 5

1-(2-Aminopropyl)-1,4-dihydro-indeno[1,2-c]pyrazol-6-ol

Step A: 2-Hydroxymethylene-5-methoxy-1-indanone

To a mixture of sodium methoxide (1.2 g, 22 mmol) in THF (20 mL) was added ethyl formate (1.6 g, 22 mmol) and 5-methoxy-1-indanone (3.24 g, 19.7 mmol) and the mixture stirred for 16 h at 23° C. The reaction mixture was added to aqueous HCl (0.1 N) and extracted with a mixture (1:1) of ethyl acetate and ether (2×20 mL). The combined organic extracts were dried (Na$_2$SO$_4$) and concentrated to a residue, which was purified by chromatography (silica, 40% ethyl acetate in hexanes) to give an oil (2.6 g, 69%): $^1$H NMR (CDCl$_3$) δ 7.81 (d, J=9.6 Hz, 1H), 7.47 (s, 1H), 7.00 (m, 2H), 3.94 (s, 3H), 3.9 (m, 2H); MS m/z 191 [M+H]$^+$.

Step B: 2-(6-Methoxy-4H-indeno[1,2-c]pyrazol-1-yl)-1-methylethylamine

To a solution of the product from Step A (1.9 g, 10 mmol) in ethanol (20 mL) was added a 1 N solution of HCl in a 1:1 mixture of methanol and ethanol followed by 2-aminopropylhydrazine (0.9 g, 10 mmol) and the solution was heated to reflux for 16 h. The solution was allowed to cool, poured into aqueous NaHCO$_3$, extracted with ethyl acetate (2×20 mL), dried (Na$_2$SO$_4$) and concentrated. The crude material was taken up in 0.1 N HCl and washed with ether (2×20 mL), basified by the addition of NaHCO$_3$ and extracted with ethyl acetate (2×20 mL). The combined organic extracts were dried (Na$_2$SO$_4$) and concentrated to a residue, which was purified by chromatography (silica, 10% methanol in dichloromethane) to furnish an oil (0.48 g, 20%); MS m/z 244 [M+H]$^+$.

Step C: [1-(6-Methoxy-4H-indeno[1,2-c]pyrazol-1-yl)-1-methylethyl]-carbamic acid 9H-fluoren-9-ylmethyl ester To a mixture of the product of Step B (0.24 g, 1.0 mmol), NaHCO$_3$ (1 g, 12 mmol), 1,4-dioxane (10 mL), and water (2 mL) was added FMOCCl (1 g, 3.7 mmol). The mixture was stirred for 14 h at 23° C., then poured into aqueous NaHCO$_3$, extracted with ethyl acetate (2×20 mL), dried (MgSO$_4$) and concentrated to a residue, which was purified by chromatography (silica, 35% ethyl acetate in hexanes) to afford an oil (0.23 g, 50%): $^1$H NMR (CDCl$_3$) δ 7.75 (d, J=6 Hz, 2H), 7.5 (m, 3H), 7.43 (s, 1H), 7.37 (m, 2H), 7.27 (m, 2H), 7.04 (s, 1H), 6.85 (m, 1H), 5.4 (bs, 1H), 4.5–4.3 (m, 4H), 4.2 (s, 1H), 4.1 (s, 1H), 3.78 (s, 3H), 3.53 (s, 2H), 1.23 (m, 3H); MS m/z 466 [M+H]$^+$.

Step D: 2-(6-Methoxy-4H-indeno[1,2-c]pyrazol-1-yl)-1-methylethylamine

The product from Step C (0.23 g, 0.5 mmol) was dissolved in a mixture of piperidine and DMF (1:4, 5 mL). The solution was stirred for 10 minutes, poured into aqueous NaHCO$_3$, extracted with ethyl acetate (2×20 mL), dried (Na$_2$SO$_4$) and concentrated. The crude product was purified by chromatography (silica, 10% methanol in dichloromethane) to give an oil (0.095 g, 78%): $^1$H NMR (CDCl$_3$) δ 7.44 (d, J=7.8 Hz, 2H), 7.41 (s, 1H), 7.08 (d, J=1.8 Hz, 1H), 6.88 (dd, J=7.8, 1.8 Hz, 1H), 4.30 (dd, J=7.8, 4.8 Hz, 1H), 4.18 (dd, J=7.8, 4.8 Hz, 1H), 3.85 (s, 3H), 3.55 (m, 2H), 3.54 (s, 2H), 1.23 (m, 3H); MS m/z 244 [M+H]$^+$.

Step E: 1-(2-Aminopropyl)-1,4-dihydro-indeno[1,2-c]pyrazol-6-ol

To a solution of the product from Step D (0.56 g, 0.23 mmol) in 1,2-dichloroethane (10 mL) was added boron tribromide-methylsulfide complex in THF solution (1.0M, 0.5 mL, 0.5 mmol) and the solution heated to reflux for 16 h. The solution was allowed to cool, poured into aqueous NaHCO$_3$, extracted with chloroform (2×20 mL), dried (Na$_2$SO$_4$) and concentrated. The crude product was purified by chromatography (silica, 20% methanol in dichloromethane) to give a solid (0.007 g, 13%): $^1$H NMR (CDCl$_3$) δ 7.39 (m, 2H), 7.00 (s, 1H), 6.79 (dd, J=8.4, 2.4 Hz, 1H), 4.30 (dd, J=13.8, 4.8 Hz, 1H), 4.14 (dd, J=13.8, 7.8 Hz, 1H), 3.55 (m, 1H), 3.48 (bm, 4H), 1.19 (d, J=6.6 Hz, 3H); MS m/z 230 [M+H]$^+$.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of controlling normal or elevated intraocular pressure or glaucoma comprising administering to a patient a pharmaceutically effective amount of a composition comprising at least one compound of Formula I:

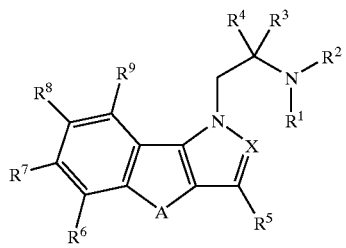

wherein $R^1$ and $R^2$ are hydrogen; or $R^1$ is a hydrogen or a substituted or unsubstituted alkyl group when $R^2$ and $R^3$ are part of a heterocycle;

$R^3$ and $R^4$ are independently chosen from hydrogen, $C_{1-4}$alkyl, or $R^3$, $R^4$ and the carbon atom to which they are attached form a cyclopropyl ring, or $R^2$ and $R^3$ together represent $(CH_2)_m$ and with the nitrogen linked to $R^2$ to form pyrrolidine;

$R^5$ is chosen from hydrogen, halogen, or a substituted or unsubstituted alkyl group;

$R^6$–$R^9$ are independently chosen from hydrogen, halogen, a substituted or unsubstituted alkyl group, a substituted or unsubstituted alkoxy group, or hydroxyl wherein at least one of $R^6$–$R^9$ is a hydroxyl;

A is $CH_2CH_2$, $CH=CH$, or $CR^{10}R^{11}$;

X is N;

$R^{10}$ and $R^{11}$ are independently hydrogen, a substituted or unsubstituted alkyl group, or halogen;

m is 3;

or pharmaceutically acceptable salts or solvates thereof.

2. The method of claim 1, wherein $R^1$ and $R^2$ are hydrogen; or $R^1$ is a hydrogen or a $C_{1-4}$alkyl group when $R^2$ and $R^3$ are part of a heterocycle;

$R^3$ and $R^4$ are independently chosen from hydrogen, $C_{1-4}$alkyl, or $R^3$, $R^4$ and the carbon atom to which they are attached form a cyclopropyl ring, or $R^2$ and $R^3$ together represent $(CH_2)_m$ and with the nitrogen linked to $R^2$ to form pyrrolidine;

$R^5$ is chosen from hydrogen, halogen, $C_{1-4}$alkyl, or $C_{1-4}$alkyl substituted with halogen;

$R^6$–$R^9$ are independently chosen from hydrogen, halogen, $C_{1-4}$ alkyl, $C_{1-4}$ alkoxy, hydroxyl, or $C_{1-4}$ alkyl substituted with halogen wherein at least one $R^6$–$R^9$ is a hydroxyl;

A is $CH_2CH_2$, $CH=CH$, or $CR^{10}R^{11}$;

X is N;

$R^{10}$ and $R^{11}$ are independently hydrogen, $C_{1-4}$alkyl, or halogen;

m is 3;

or pharmaceutically acceptable salts and solvates thereof.

3. The method of claim 1, wherein said $R^2$ and $R^3$ represent $(CH_2)_m$ and with the nitrogen linked to $R^2$ to form pyrrolidine or said $R^3$ and $R^4$ together form a cyclopropyl ring.

4. The method of claim 1, wherein $R^1$ and $R^2$ are hydrogen;

$R^3$ is $C_{1-4}$alkyl or $R^2$ and $R^3$ together is $(CH_2)_3$ to form pyrrolidine;

$R^4$ is hydrogen;

$R^5$ is chosen from hydrogen, halogen, $C_{1-4}$alkyl, or $C_{1-4}$alkyl substituted by halogen;

$R^6$–$R^9$ are independently chosen from hydrogen, halogen, $C_{1-4}$alkyl, $C_{1-4}$alkoxy, hydroxyl, or $C_{1-4}$alkyl substituted with halogen wherein at least one of $R^6$–$R^9$ is a hydroxyl;

A is $CH=CH$ or $CH_2CH_2$; and

X is N;

or pharmaceutically acceptable salts and solvates thereof.

5. The method of claim 1, wherein:

$R^1$ and $R^2$ are hydrogen;

$R^3$ is $C_{1-4}$alkyl;

$R^4$ is hydrogen;

$R^5$ is chosen from hydrogen or $C_{1-4}$alkyl;

$R^6$ and $R^7$ are hydrogen, halogen, or $C_{1-4}$alkyl;

$R^8$ and $R^9$ are independently chosen from hydrogen, halogen, or hydroxyl;

A is $CH=CH$ or $CH_2CH_2$; and

X is N;

or pharmaceutically acceptable salts and solvates thereof.

6. The method of claim 1, wherein said compound is:

1-(2-Aminopropyl)-4,5-dihydro-1H-benzo[g]indazol-8-ol;

1-(2-Aminopropyl)-1H-benzo[g]indazol-8-ol;

1-(2-Aminopropyl)-1H-benzo[g]indazol-7-ol;

2-(8-Methoxy-benzo[g]indazol-1-yl)-1-methylethylamine;

1-(2-Aminopropyl)-1,4-dihydro-indeno[1,2-c]pyrazol-6-ol; or 1-(2-Aminopropyl)-4,4-dimethyl-2,4-dihydro-indeno[1,2-c]pyrazol-7-ol; or combinations thereof.

7. The method of claim 1, wherein said composition is present in a sterile suspension or solution, or in a sterile ointment formulation or sterile gel formulation.

8. The method of claim 1, wherein $R^1$, $R^2$, $R^4$–$R^7$, and $R^9$ are hydrogen, $R^3$ is $CH_3$, $R^8$ is OH, A is CH=CH and X is N.

9. The method of claim 1, wherein $R^1$, $R^2$, $R^4$–$R^7$, and $R^9$ are hydrogen, $R^3$ is $C_{1-4}$alkyl, $R^8$ is OH, A is CH=CH, and X is N.

10. The method of claim 1, wherein A is $CH_2CH_2$.

11. The method of claim 1, wherein A is $CR^{10}R^{11}$.

12. The method of claim 1, wherein at least two of $R^6$–$R^9$ is OH.

13. The method of claim 1, wherein at least one of $R^6$–$R^9$ is a substituted or unsubstituted alkyl group.

14. The method of claim 1, wherein at least one $R^6$–$R^9$ is a substituted or unsubstituted alkoxy group.

15. The method of claim 1, wherein $R^1$ and $R^2$ are hydrogen.

16. The method of claim 11, wherein $R^1$ and $R^2$ are hydrogen.

17. The method of claim 12, wherein $R^1$ and $R^2$ are hydrogen.

18. A method of controlling normal or elevated intraocular pressure or glaucoma comprising administering to a patient a pharmaceutically effective amount of a composition comprising at least one compound of Formula I:

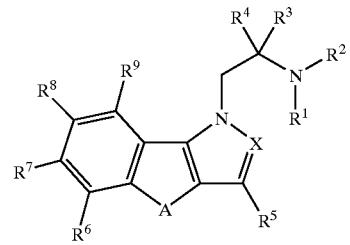

wherein $R^1$ and $R^2$ are hydrogen; or $R^2$ is a hydrogen or a substituted or unsubstituted alkyl group when $R^2$ and $R^3$ are part of a heterocycle;

$R^3$ and $R^4$ are independently chosen from hydrogen, $C_{1-4}$alkyl, or $R^3$, $R^4$ and the carbon atom to which they are attached form a cyclopropyl ring, or $R^2$ and $R^3$ together represent $(CH_2)_m$ and with the nitrogen linked to $R^2$ to form pyrrolidine;

$R^5$ is halogen;

$R^6$–$R^9$ are independently chosen from hydrogen, halogen, a substituted or unsubstituted alkyl group, a substituted or unsubstituted alkoxy group, or hydroxyl;

A is $CH_2CH_2$, CH=CH, or $CR^{10}R^{11}$;

X is N;

$R^{10}$ and $R^{11}$ are independently hydrogen, a substituted or unsubstituted alkyl group, or halogen;

m is 3;

or pharmaceutically acceptable salts or solvates thereof.

19. The method of claim 1, wherein said method is for treating glaucoma.

20. The method of claim 1, wherein said method is for treating normal or elevated intraocular pressure.

21. The method of claim 18, wherein said method is for treating glaucoma.

22. The method of claim 18, wherein said method is for treating normal or elevated intraocular pressure.

* * * * *

UNITED STATES PATENT AND TRADEMARK OFFICE
CERTIFICATE OF CORRECTION

PATENT NO. : 6,884,816 B2
DATED : April 26, 2005
INVENTOR(S) : May et al.

It is certified that error appears in the above-identified patent and that said Letters Patent is hereby corrected as shown below:

Column 17,
Line 32, "claim 1" should read -- claim 10 --.

Column 18,
Line 13, "or $R^2$ is a hydrogen" should read -- or $R^1$ is a hydrogen --.

Signed and Sealed this

Fifth Day of July, 2005

JON W. DUDAS
*Director of the United States Patent and Trademark Office*